US005695480A

United States Patent [19]
Evans et al.

[11] Patent Number: 5,695,480
[45] Date of Patent: Dec. 9, 1997

[54] EMBOLIZING COMPOSITIONS

[75] Inventors: Scott Evans, Santa Ana; Michael L. Jones, Capistrano Beach, both of Calif.; Richard Greff, St. Petersburg, Fla.

[73] Assignee: Micro Therapeutics, Inc., San Clemente, Calif.

[21] Appl. No.: 688,050

[22] Filed: Jul. 29, 1996

[51] Int. Cl.$^6$ .................................................. A61M 5/00
[52] U.S. Cl. ........................................................ 604/264
[58] Field of Search ............................................ 604/264

[56] References Cited

U.S. PATENT DOCUMENTS

| | | | |
|---|---|---|---|
| 3,527,224 | 9/1970 | Rabinowitz et al. | 604/264 |
| 3,591,676 | 7/1971 | Hawkins et al. | 604/264 |
| 4,079,124 | 3/1978 | Winchell | 424/4 |
| 4,795,741 | 1/1989 | Leshchiner et al. | 514/21 |
| 5,202,352 | 4/1993 | Okada et al. | 514/475 |
| 5,443,454 | 8/1995 | Tanabe et al. | 604/264 |

OTHER PUBLICATIONS

Casarett and Doull's *Toxicology*, Amdur et al., Editors, Pergamon Press, New York, pp. 661–664 (1975).

Castaneda–Zuniga, et al., "Interventional Radiology", in *Vascular Embolotherapy, Part 1*, 1:9–32, William & Wilkins, Publishers (1992).

Kinugasa, et al., "Direct Thrombosis of Aneurysms with Cellulose Acetate Polymer", *J. Neurosurg.*, 77:501–507 (1992).

Kinugasa, et al., "Early Treatment of Subarachnoid Hemorrhage After Preventing Rerupture of an Aneurysm", *J. Neurosurg.*, 83:34–41 (1995).

Kinugasa, et al., "Prophylactic Thrombosis to Prevent New Bleeding and to Delay Aneurysm Surgery", *Neurosurg.*, 36:661 (1995).

Mandai, et al., "Direct Thrombosis of Aneurysms with Cellulose Acetate Polymer", *J. Neurosurg.*, 77:497–500 (1992).

Taki, et al., "Selection and Combination of Various Endovascular Techniques in the Treatment of Giant Aneurysms", *J. Neurosurg.*, 77:37–42 (1992).

Taki, K., "Posibility and Limit of Intravascular Surgery", *Medical Tribune*, pp. 46–47, Oct. 26, 1989.

*Primary Examiner*—Terressa Mosley
*Attorney, Agent, or Firm*—Burns, Doane, Swecker & Mathis, L.L.P.

[57] ABSTRACT

Disclosed are novel compositions for embolizing blood vessels which are particularly suited for treating vascular lesions via catheter delivery. In one embodiment, the compositions of this invention comprise a biocompatible polymer, a biocompatible solvent and a biocompatible water insoluble contrast agent characterized by having an average particle size of less than about 10 µm.

In another embodiment, the biocompatible polymer in these compositions is replaced with a biocompatible prepolymer.

46 Claims, No Drawings

EMBOLIZING COMPOSITIONS

BACKGROUND OF THE INVENTION

Field of the Invention

This invention is directed to novel compositions for embolizing blood vessels which are particularly suited for treating vascular lesions via catheter delivery of the composition. In particular, the compositions of this invention comprise a biocompatible polymer, a biocompatible solvent and a biocompatible water insoluble contrast agent characterized by having an average particle size of about 10 μm or less.

REFERENCES

The following publications are cited in this application as superscript numbers:

1. Mandai, et al., "Direct Thrombosis of Aneurysms with Cellulose Acetate Polymer", J. Neurosurg., 77:497–500 (1992)
2. Kinugasa, et al., "Direct Thrombosis of Aneurysms with Cellulose Acetate Polymer", J. Neurosurg., 77:501–507 (1992)
3. Casarett and Doull's Toxicology, Amdur et al., Editors, Pergamon Press, New York, pp. 661–664 (1975)
4. Greff, et al., U.S. patent application Ser. No. 08/507, 863 for "Novel Compositions for Use in Embolizing Blood Vessels", filed Jul. 27, 1995
5. Greff, et al., U.S. patent application Ser. No. 08/508, 248 for "Cellulose Diacetate Compositions for Use in Embolizing Blood Vessels", filed Jul. 27, 1995
6. Kinugasa, et at., "Early Treatment of Subarachnoid Hemorrhage After Preventing Rerupture of an Aneurysm", J. Neurosurg., 83:34–41 (1995)
7. Kinugasa, et al., "Prophylactic Thrombosis to Prevent New Bleeding and to Delay Aneurysm Surgery", Neurosurg., 36:661 (1995)
8. Taki, et at., "Selection and Combination of Various Endovascular Techniques in the Treatment of Giant Aneurysms", J. Neurosurg., 77:37–42 (1992)
9. Evans, et at., U.S. patent application Ser. No. 08/655, 822 for "Novel Compositions for Use in Embolizing Blood Vessels", flied May 31, 1996.
10. Castaneda-Zuniga, et al., Interventional Radiology, in Vascular Embolotherapy, Part 1, 1:9–32, Williams & Wilkins, Publishers (1992)
11. Rabinowitz, et al., U.S. Pat. No. 3,527,224, for "Method of Surgically Bonding Tissue Together", issued Sep. 8, 1970
12. Hawkins, et al., U.S. Pat. No. 3,591,676, for "Surgical Adhesive Compositions", issued Jul. 6, 1971
13. Evans, et at., U.S. patent application Ser. No. 08/655, 987, for "Methods for the Reversible Sterilization of Male Mammals", filed May 31, 1996 as Attorney Docket No. 018413-007
14. Evans, et at., U.S. patent application Ser. No. 08/656, 394, for "Methods for the Reversible Sterilization of Female Mammals", filed May 31, 1996 as Attorney Docket No. 018413-014

All of the above references are herein incorporated by reference in their entirety to the same extent as if each individual reference was specifically and individually indicated to be incorporated herein by reference in its entirety.

STATE OF THE ART

Embolization of blood vessels is conducted for a variety of purposes including the treatment of tumors, the treatment of lesions such as aneurysms, arteriovenous malformations (AVM), arteriovenous fistula (AVF), uncontrolled bleeding and the like.

Embolization of blood vessels is preferably accomplished via catheter techniques which permit the selective placement of the catheter at the vascular site to be embolized. In this regard, recent advancements in catheter technology as well as in angiography now permit neuro endovascular intervention including the treatment of otherwise inoperable lesions. Specifically, development of microcatheters and guide wires capable of providing access to vessels as small as 1 mm in diameter allows for the endovascular treatment of many lesions.

Endovascular treatment regimens preferably include the use of a water insoluble, radiopaque contrast agent in the embolizing compositions in order that the physician can visualize delivery of the composition to the vascular site via conventional techniques such as fluoroscopy.[1-8] Additionally, the use of water insoluble constrast agents ise beneficial during posttreatment procedures to visualize the embolized mass during, for example surgery, or to monitor the disease condition and/or retreatment purposes. Visualization is particularly necessary when using catheter delivery techniques in order to ensure both that the composition is being delivered to the intended vascular site and that the requisite amount of composition is delivered. The latter requirement is particularly critical in the treatment of aneurysms where only the aneurysm sac is intended to be filled while leaving the adjoining blood vessel unaffected. Accordingly, in such treatments, the amount of embolic composition delivered is selected to substantially fill but not overflow the aneurysm sac. If less than this amount of embolic composition is delivered to the aneurysm sac, the patient will be left with an active aneurysm which, in some cases, can be more dangerous than the untreated aneurysm. If more than this amount of embolic composition is delivered, the composition will overflow into the adjoining blood vessel which can then embolize this blood vessel as well as the aneurysm. In the case where the affected blood vessel is in or leads to a critical body organ, e.g., the brain, permanent damage due to blood flow cessation will result.

When delivered by catheter, the embolic compositions preferably comprise a biocompatible solvent, a biocompatible polymer and the water insoluble contrast agent. The biocompatible solvent is miscible or soluble in blood or other body fluid and also solubilizes the biocompatible polymer during delivery. The biocompatible polymer is selected to be soluble in the biocompatible solvent but insoluble in blood or other body fluid. The water insoluble contrast agent is suspended in the composition and, as above, permits the physician to fluoroscopically visualize catheter delivery of this composition. Upon contact with the blood or other body fluid, the biocompatible solvent dissipates from the embolic composition whereupon the biocompatible polymer precipitates in the presence of the water insoluble contrast agent and embolizes the blood vessel.

In practice, complications in this procedure have, however, been found including the fact that often the fluoroscopic visibility of these compositions is inconsistent during catheter delivery. Such inconsistency resulted in either the under filling or overfilling of the vascular space leading invariably to less than a satisfactory result.

While efforts have been made to improve the consistency of the fluoroscopic visibility of these compositions, such efforts were hindered by a lack of a clear understanding of the underlying cause of this problem. In view of the above, there is an ongoing need to enhance the fluoroscopic visibility of polymer compositions used for embolizing vascular sites.

SUMMARY OF THE INVENTION

This invention is directed to the novel and unexpected discovery that the particle size of the water insoluble contrast agent is critical to providing an embolic composition which can be consistently visualized during catheter delivery of the composition. Specifically, it has been found that fluoroscopic visualization of the embolic composition can be consistently achieved by employing a water insoluble contrast agent having an average particle size of about 10 µm or less.

Without being limited to any theory, it is now believed that during catheter delivery of embolic compositions having average particle sizes of greater than 10 µm, a portion of the contrast agent is not maintained in the embolic composition as delivered to the vascular site due to, for example, settling of the water insoluble contrast agent from suspension either before and/or during catheter delivery, adherence of the large particle size contract agents to the walls of the catheter delivery system, and the like. It is further believed that the narrow passages of the catheter delivery system coupled with the delivery protocol which requires that the contrast agent be maintained in suspension for prolonged periods of time aggravates this situation. In any event, the inventors believe that it is this failure to maintain a minimum amount of contrast agent in the injected embolic composition which leads to inconsistent fluoroscopic visualization during catheter delivery.

Accordingly, in one of its composition aspects, this invention is directed to a composition comprising:

(a) from about 2.5 to about 8.0 weight percent of a biocompatible polymer;

(b) from about 10 to about 40 weight percent of a water insoluble, biocompatible contrast agent having an average particle size of about 10 µm or less; and (c) from about 52 to about 87.5 weight percent of a biocompatible solvent wherein the weight percent of the polymer, contrast agent and biocompatible solvent is based on the total weight of the complete composition.

In one of its method aspects, this invention is directed to a method for embolizing a blood vessel by delivering via a catheter into said blood vessel a composition comprising:

(a) from about 2.5 to about 8.0 weight percent of a biocompatible polymer;

(b) from about 10 to about 40 weight percent of a water insoluble, biocompatible contrast agent having an average particle size of about 10 µm or less;

(c) from about 52 to about 87.5 weight percent of a biocompatible solvent wherein the weight percent of the polymer, contrast agent and biocompatible solvent is based on the total weight of the complete composition under conditions wherein a precipitate is formed which embolizes the blood vessel.

In another embodiment, the biocompatible polymer composition can be replaced with a biocompatible prepolymer composition containing a biocompatible prepolymer. In this embodiment, this invention is directed to a composition comprising:

(a) a biocompatible prepolymer;

(b) a biocompatible, water insoluble contrast agent having an average particle size of about 10 µm or less; and (c) optionally, a biocompatible solvent.

In addition, this invention is also directed to a method for embolizing a vascular site by delivering via a catheter into said blood vessel a composition comprising:

(a) a biocompatible prepolymer;

(b) a biocompatible, water insoluble contrast agent having an average particle size of about 10 µm or less; and (c) optionally a biocompatible solvent wherein said delivery is conducted under conditions wherein said prepolymer polymerizes in situ, in the presence of the water insoluble contrast agent, at said vascular site thereby embolizing the blood vessel.

In a preferred embodiment, the water insoluble, biocompatible contrast agent is selected from the group consisting of barium sulfate, tantalum powder and tantalum oxide. In still a further preferred embodiment, the biocompatible solvent is dimethylsulfoxide (DMSO), ethanol or acetone.

In one of its kit aspects, this invention is directed to a kit of parts comprising:

(a) a polymer composition comprising a biocompatible polymer, a biocompatible solvent and a biocompatible, water insoluble contrast agent having an average particle size of about 10 µm or less; and (b) a catheter.

In another of its kit aspects, this invention is directed to a kit of parts comprising:

(a) a prepolymer composition comprising a biocompatible prepolymer, a biocompatible, water insoluble contrast agent having an average particle size of about 10 µm or less, and, optionally, a biocompatible solvent; and (b) a catheter.

In a preferred embodiment, the kit further comprises a microballoon catheter to attenuate or arrest blood flow.

DETAILED DESCRIPTION OF THE INVENTION

This invention is directed to novel compositions for embolizing blood vessels which are particularly suited for treating vascular lesions via catheter delivery of the composition.

However, prior to discussing this invention in further detail, the following terms will first be defined:

The term "embolizing" refers to a process wherein a material is injected into a blood vessel which, in the case of, for example, aneurysms, fills or plugs the aneurysm sac and/or encourages clot formation so that blood flow into the aneurysm ceases, and in the case of AVM's and AVF's forms a plug or clot to control/reroute blood flow to permit proper tissue perfusion. Embolization of the blood vessel is, therefore, important in preventing/controlling bleeding due to lesions (e.g., organ bleeding, gastrointestinal bleeding, vascular bleeding as well as bleeding associated with an aneurysm). In addition, embolization can be used to ablate diseased tissue (e.g., tumors, etc.) by cutting off its blood supply.

The term "biocompatible polymer" refers to polymers which, in the amounts employed, are non-toxic, chemically inert, and substantially non-immunogenic when used internally in the patient and which are substantially insoluble in blood. Suitable biocompatible polymers include, by way of example, cellulose acetates[2,6-7] (including cellulose diacetate[5]), ethylene vinyl alcohol copolymers[4,8], hydrogels (e.g., acrylics), polyacrylonitrile, polyvinylacetate, cellulose acetate butyrate, nitrocellulose, copolymers of urethane/carbonate, copolymers of styrene/maleic acid, and mixtures thereof[9]. Preferably, the biocompatible polymer is also non-inflammatory when employed in situ.

The particular biocompatible polymer employed is not critical and is selected relative to the viscosity of the resulting polymer solution, the solubility of the biocompatible polymer in the biocompatible solvent, and the like. Such factors are well within the skill of the art.

Preferred biocompatible polymers include cellulose diacetate and ethylene vinyl alcohol copolymer. Cellulose diacetate polymers are either commercially available or can be prepared by art recognized procedures. In a preferred embodiment, the number average molecular weight, as determined by gel permeation chromatography, of the cellulose diacetate composition is from about 25,000 to about 100,000 more preferably from about 50,000 to about 75,000 and still more preferably from about 58,000 to 64,000. The weight average molecular weight of the cellulose diacetate composition, as determined by gel permeation chromatography, is preferably from about 50,000 to 200,000 and more preferably from about 100,000 to about 180,000. As is apparent to one skilled in the art, with all other factors being equal, cellulose diacetate polymers having a lower molecular weight will impart a lower viscosity to the composition as compared to higher molecular weight polymers. Accordingly, adjustment of the viscosity of the composition can be readily achieved by mere adjustment of the molecular weight of the polymer composition.

Ethylene vinyl alcohol copolymers comprise residues of both ethylene and vinyl alcohol monomers. Small amounts (e.g., less than 5 mole percent) of additional monomers can be included in the polymer structure or grafted thereon provided such additional monomers do not alter the embolizing properties of the composition. Such additional monomers include, by way of example only, maleic anhydride, styrene, propylene, acrylic acid, vinyl acetate and the like.

Ethylene vinyl alcohol copolymers are either commercially available or can be prepared by art recognized procedures. Preferably, the ethylene vinyl alcohol copolymer composition is selected such that a solution of 6 weight percent of the ethylene vinyl alcohol copolymer, 35 weight percent of a tantalum contrast agent in DMSO has a viscosity equal to or less than 60 centipoise at 20° C. As is apparent to one skilled in the art, with all other factors being equal, copolymers having a lower molecular weight will impart a lower viscosity to the composition as compared to higher molecular weight copolymers. Accordingly, adjustment of the viscosity of the composition as necessary for catheter delivery can be readily achieved by mere adjustment of the molecular weight of the copolymer composition.

As is also apparent, the ratio of ethylene to vinyl alcohol in the copolymer affects the overall hydrophobicity/hydrophilicity of the composition which, in turn, affects the relative water solubility/insolubility of the composition as well as the rate of precipitation of the copolymer in an aqueous solution (e.g., blood). In a particularly preferred embodiment, the copolymers employed herein comprise a mole percent of ethylene of from about 25 to about 60 and a mole percent of vinyl alcohol of from about 40 to about 75. These compositions provide for requisite precipitation rates suitable for use in embolizing blood vessels.

The term "water insoluble contrast agent" refers to a water insoluble (i.e., has a water solubility of less than 0.01 mg/ml at 20° C.), radiopaque material capable of being monitored during injection into a mammalian subject by, for example, radiography. Examples of water insoluble contrast agents include tantalum, tantalum oxide and barium sulfate, which are commercially available in the proper form for in vivo use. Methods for preparing such water insoluble biocompatible contrast agents having an average particle size of about 10 μm or less are described below. Other water insoluble contrast agents include gold, tungsten and platinum.

The term "biocompatible solvent" refers to an organic material liquid at least at body temperature of the mammal in which the biocompatible polymer is soluble and, in the amounts used, is substantially non-toxic. Suitable biocompatible solvents include, by way of example, dimethylsulfoxide, analogues/homologues of dimethylsulfoxide, ethanol, acetone, and the like. Aqueous mixtures with the biocompatible solvent can also be employed provided that the amount of water employed is sufficiently small that the dissolved polymer precipitates upon contact with the blood. Preferably, the biocompatible solvent is dimethylsulfoxide.

The term "encapsulation" as used relative to the contrast agent being encapsulated in the polymer precipitate is not meant to infer any physical entrapment of the contrast agent within the precipitate much as a capsule encapsulates a medicament. Rather, this term is used to mean that an integral coherent precipitate forms which does not separate into individual components.

The term "biocompatible prepolymer" refers to materials which polymerize in situ to form a polymer and which, in the amounts employed, are non-toxic, chemically inert, and substantially non-immunogenic when used internally in the patient and which are substantially insoluble in blood. Suitable biocompatible prepolymers include, by way of example, cyanoacrylates[10,11,12], hydroxyethyl methacrylate, silicon prepolymers, and the like. The prepolymer can either be a monomer or a reactive oligomer[12]. Preferably, the biocompatible prepolymer is also non-inflammatory when employed in situ.

Compositions

The polymer or prepolymer compositions employed in the methods of this invention are prepared by conventional methods whereby each of the components is added and the resulting composition mixed together until the overall composition is substantially homogeneous.

For example, polymer compositions can be prepared by adding sufficient amounts of the biocompatible polymer to the biocompatible solvent to achieve the effective concentration for the polymer composition. Preferably, the polymer composition will comprise from about 2.5 to about 8.0 weight percent of the biocompatible polymer composition based on the total weight of the polymer composition and more preferably from about 4 to about 5.2 weight percent. If necessary, gentle heating and stirring can be used to effect dissolution of the biocompatible polymer into the biocompatible solvent, e.g., 12 hours at 50° C.

Sufficient amounts of the contrast agent are then added to the biocompatible solvent to achieve the effective concentration for the complete composition. Preferably, the composition will comprise from about 10 to about 40 weight percent of the contrast agent and more preferably from about 20 to about 40 weight percent and even more preferably about 30 weight percent. Insofar as the contrast agent is not soluble in the biocompatible solvent, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm). In one preferred embodiment, the appropriate particle size of the contrast agent is prepared, for example, by fractionation. In such an embodiment, a water insoluble contrast agent such as tantalum having an average particle size of less than about 20 microns is added to an organic liquid such as ethanol (absolute) preferably in a clean environment. Agitation of the resulting suspension followed by settling for approximately 40 seconds permits the larger particles to settle faster. Removal of the upper portion of the organic liquid followed by separation of the liquid from the particles results in a reduction of the particle size which is confirmed under an optical microscope. The process is optionally repeated until a desired average particle size is reached.

The particular order of addition of components to the biocompatible solvent is not critical and stirring of the resulting suspension is conducted as necessary to achieve homogeneity of the composition. Preferably, mixing/stirring of the composition is conducted under an anhydrous atmosphere at ambient pressure. The resulting composition is heat sterilized and then stored preferably in sealed amber bottles or vials until needed.

Each of the polymers recited herein is commercially available but can also be prepared by methods well known in the art. For example, polymers are typically prepared by conventional techniques such as radical, thermal, UV, γ irradiation, or electron beam induced polymerization employing, as necessary, a polymerization catalyst or polymerization initiator to provide for the polymer composition. The specific manner of polymerization is not critical and the polymerization techniques employed do not form a part of this invention.

In order to maintain solubility in the biocompatible solvent, the polymers described herein are preferably not cross-linked.

Prepolymer compositions can be prepared by adding sufficient amounts of the contrast agent to the solution (e.g., liquid prepolymer) to achieve the effective concentration for the complete polymer composition. Preferably, the prepolymer composition will comprise from about 10 to about 40 weight percent of the contrast agent and more preferably from about 20 to about 40 weight percent and even more preferably about 30 weight percent. When the contrast agent is not soluble in the biocompatible prepolymer composition, stirring is employed to effect homogeneity of the resulting suspension. In order to enhance formation of the suspension, the particle size of the contrast agent is preferably maintained at about 10 μm or less and more preferably at from about 1 to about 5 μm (e.g., an average size of about 2 μm).

When the prepolymer is liquid (as in the case of polyurethanes), the use of a biocompatible solvent is not absolutely necessary but may be preferred to provide for an appropriate viscosity, etc. in the embolic composition. Preferably, when employed, the biocompatible solvent will comprise from about 30 to about 90 weight percent of the biocompatible prepolymer composition based on the total weight of the prepolymer composition and more preferably from about 60 to about 80 weight percent. When a biocompatible solvent is employed, the prepolymeric composition typically comprises from about 10 to about 50 weight percent of the prepolymer based on the total weight of the composition.

In a particularly preferred embodiment, the prepolymer is cyanoacrylate which is preferably employed in the absence of a biocompatible solvent. When so employed, the cyanoacrylate adhesive is selected to have a viscosity of from about 5 to about 20 centipoise at 20° C.

The particular order of addition of components is not critical and stirring of the resulting suspension is conducted as necessary to achieve homogeneity of the composition. Preferably, mixing/stirring of the composition is conducted under an anhydrous atmosphere at ambient pressure. The resulting composition is sterilized and then stored preferably in sealed amber bottles or vials until needed.

Methods

The compositions described above can then be employed in methods for the catheter assisted embolization of mammalian blood vessels. In such methods, a sufficient amount of this composition is introduced into the selected blood vessel via a catheter delivery means under fluoroscopy so that upon precipitation of the polymer or polymerization of the prepolymer, the blood vessel is embolized. The particular amount of embolizing composition employed is dictated by the total volume of the vasculature to be embolized, the concentration of polymer/prepolymer in the composition, the rate of precipitation (solids formation) of the polymer, etc. Such factors are well within the skill of the art.

One particularly preferred method for catheter delivering the embolizing compositions of this invention to the selected vascular site is via a small diameter medical catheter. The particular catheter employed is not critical provided that polymeric catheter components are compatible with the embolizing composition (i.e., the catheter components will not readily degrade in the embolizing composition). In this regard, it is preferred to use polyethylene in the catheter components because of its inertness in the presence of the embolizing composition described herein. Other materials compatible with the embolizing compositions can be readily determined by the skilled artisan and include, for example, other polyolefins, fluoropolymers (e.g., Teflon™), silicone, etc.

When delivered by catheter, the injection rate dictates, in part, the form of the precipitate at the vascular site. Specifically, low injection rates of approximately 0.05 to 0.3 cc/minute will provide for a precipitate in the form of a kernel or nodule which is particularly beneficial for site specific embolization because the precipitate forms primarily at the point of injection. Contrarily, high injection rates of about 0.1 to 0.5 or more cc/several seconds (e.g., up to 10 seconds) will provide for a filament like mass projecting downstream from the catheter tip which may be particularly beneficial for providing the embolizing agent deep into the vascular tree. Such procedures are suitable for embolizing tumor masses. However, too rapid an injection of DMSO into the vascular site can cause vascular spasms and, accordingly, should be avoided and/or the use of antispasmodic drugs such as papaverine can be employed if spasms arise.

One particularly preferred method for the catheter injection of the composition of this invention is as follows:

1. Microcatheter placement in vivo is confirmed by injection of water soluble contrast agent;
2. The cap on the microcatheter luer hub is secured and then the water insoluble contrast agent in the composition is fully dispersed by vigorous shaking and then setting this aside;
3. Aspirate 0.8 cc of sterile DMSO into a 1 cc syringe. Remove cap from microcatheter hub. Inject 0.30 cc of DMSO for a typical 150 cm microcatheter. Remove the syringe and overfill/wash the luer hub with 0.3 cc of DMSO. Immediately place and secure the cap on the microcatheter luer hub to prevent backflow and mixing;
4. Again, shake the composition well to fully disperse the water insoluble contrast agent. Fill a 1 cc syringe with the composition through a 21 gage needle. Remove cap from microcatheter hub, fill any air space in the hub with the remaining DMSO and immediately connect the composition syringe to the catheter hub, making sure that there is no air in the hub during the connection;

5. With the composition syringe pointing up to create a sharp interfacial boundary between the DMSO and the embolic composition, slowly inject the first 0.25 cc over a 1 min. period to displace the DMSO in the microcatheter and dilute the DMSO in the blood;

6. Under fluoroscopy, the embolic composition should be visible in the distal portion of the microcatheter body. Lower the syringe tip and inject the embolic composition as the clinical situation requires. Monitor the volume of the embolic composition injected to correspond to the volume of the vascular space being filled; and 7. Upon completion of the embolic composition injection, gently aspirate with the embolic syringe to separate the catheter tip from the embolic composition mass. Wait a few seconds, release the syringe plunger and withdraw the microcatheter.

In this protocol, the dead space for the 150 cm microcatheter is about 0.32 cc.

In the case of aneurysms, the mammal is preferably rotated to place the aneurysm in a downward position to encourage displacement of aneurysmal blood.

When introduced into the vascular site, the biocompatible solvent diffuses rapidly into the blood and a solid precipitate forms which precipitate is the water insoluble polymer with the contrast agent encapsulated therein. Without being limited to any theory, it is believed that initially, a soft gel to spongy solid precipitate forms upon contact with the blood. This precipitate then restricts blood flow, entrapping red cells thereby causing clot embolization of the blood vessel.

Utility

The compositions described herein are useful in embolizing mammalian blood vessels which, in turn, can be used to prevent/control bleeding (e.g., organ bleeding, gastrointestinal bleeding, vascular bleeding, bleeding associated with an aneurysm) or to ablate diseased tissue (e.g., tumors, etc.). Accordingly, these compositions find use in human and other mammalian subjects requiring embolization of blood vessels. Additionally, these compositions can be used in the reversible sterilization of mammalian patients as described in concurrently filed applications by Evans, et al.[13,14].

It is contemplated that these compositions can be employed as a carrier for a compatible pharmaceutically active compound wherein this compound is delivered in vivo for subsequent release. Such compounds include by way of example only antibiotics, anti-inflammatory agents, chemotherapeutic agents, and the like.

The following examples are set forth to illustrate the claimed invention and are not to be construed as a limitation thereof.

EXAMPLES

Unless otherwise stated, all temperatures are in degrees Celsius. Also, in these examples and elsewhere, the following abbreviations have the following meanings:

| | |
|---|---|
| cc = | cubic centimeter |
| cm = | centimeter |
| DMSO = | dimethylsulfoxide |
| EVOH = | ethylene vinyl alcohol copolymer |
| g = | gram |
| ID = | internal diameter |
| in. = | inch |
| min. = | minute |
| mL = | milliliter |
| mm = | millimeter |
| OD = | outer diameter |
| sec. = | seconds |
| μm = | micron |

Example 1

The purpose of this example is to demonstrate that the amount of water insoluble contrast agent delivered via a small medical diameter catheter correlates to the average particle size of the contrast agent when all other factors are kept constant.

Specifically, two (2) EVOH polymer compositions, identical in all aspects except average particle size, were prepared as follows:

First Composition

A) 8 gm EVOH;

B) 30 gm tantalum having an average particle size of about 15 μm (narrow size distribution); and C) 100 mL DMSO.

Second Composition

A) 8 gm EVOH;

B) 30 gm tantalum having an average particle size of about 3 μm (narrow size distribution); and C) 100 mL DMSO.

Each composition was mixed until homogeneous.

In the second composition, the average particle size of the contrast agent was prepared by fractionation wherein tantalum, having an average particle size of less than about 20 μm, was added to ethanol (absolute) in a clean environment. Agitation of the resulting suspension was followed by settling for approximately 40 sec. to permit the larger particles to settle faster. Removal of the upper portion of the ethanol followed by separation of the liquid from the particles results in a reduction of the particle size which is confirmed under a microscope (Nikon Alphaphot™). The process was repeated, as necessary, until an average 3 μm particle size was reached.

Two identical catheters (polyolefin microcatheter, 0.036 in. OD×0.016 in. ID, dead space 0.45 cc) were each flushed with 10 cc saline solution and then primed with 0.3 cc DMSO. Two 1 cc syringes were filled with either the first or second composition described above through 21 gage needles and connected to. the luer hubs of the catheters. The catheter distal tips were submerged in warm tap water. Exactly 0.50 cc of each composition was injected into the water over a 5 min. period.

Tantalum is black and the above polymer compositions are otherwise white. Accordingly, the degree of tantalum incorporation in the injected composition is visually monitored by measuring the color characteristics of each injected composition. In the present case, the precipitate formed from each catheter was evaluated and the results of this evaluation are reported in Table I below:

TABLE I

| Average Particle Size of Tantalum in Composition | Characteristics of Precipitate Formed |
| --- | --- |
| 15 μm | white to light gray, indicating that it contained little tantalum content |
| 3 μm | dark black, indicating a high level of tantalum in the composition |

Each precipitate was then visualized under fluoroscopy. The first precipitate having a 15 μm average particle size of tantalum in the composition was barely visible, whereas visualization of the second precipitate (3 μm average particle size of tantalum in the composition) was outstanding.

Subsequent experiments on similar compositions confirmed these results. Specifically, the first composition gave a white to grayish precipitates at 5.0 and 2.0 minutes injection times whereas a 1.0 minute injection time gave a black precipitate.

The above results evidence that compositions containing a water insoluble contrast agent having an average particle size of greater than about 10 μm did not retain sufficient contrast agent in the composition delivered by catheter injection to be readily visualized when the composition was slowly injected. Rapid injection apparently minimizes settling and/or other phenomena related to the failure of the water insoluble contrast agent to be retained in the precipitate. Contrarily, the same compositions having an average particle size of about 3 μm for the water insoluble contrast agent provided acceptable results at all injection times.

It is contemplated that the embolic compositions of this invention will also possess improved flow rates and less in-catheter separation as compared to similar compositions comprising a water insoluble contrast agent having an average particle size of greater than 10 μm.

It is understood that the same procedures set forth above can be employed with compositions employing liquid prepolymers.

From the foregoing description, various modifications and changes in the composition and method will occur to those skilled in the art. All such modifications coming within the scope of the appended claims are intended to be included therein.

What is claimed is:

1. A composition comprising:
   (a) from about 2.5 to about 8.0 weight percent of a biocompatible polymer;
   (b) from about 10 to about 40 weight percent of a water insoluble, biocompatible contrast agent having an average particle size of about 10 μm or less; and
   (c) from about 52 to about 87.5 weight percent of a biocompatible solvent
   wherein the weight percent of the polymer, contrast agent and biocompatible solvent is based on the total weight of the complete composition.

2. The composition according to claim 1 wherein said biocompatible solvent is selected from the group consisting of dimethylsulfoxide, ethanol and acetone.

3. The composition according to claim 2 wherein said biocompatible solvent is dimethylsulfoxide.

4. The composition according to claim 1 wherein said water insoluble contrast agent is selected from the group consisting of tantalum, tantalum oxide, tungsten and barium sulfate.

5. The composition according to claim 3 wherein said contrast agent is tantalum.

6. The composition according to claim 1 wherein said biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

7. The composition according to claim 6 wherein said biocompatible polymer is an ethylene and vinyl alcohol copolymer.

8. The composition according to claim 7 wherein said contrast agent has an average particle size of from 1 to 10 microns.

9. A method for embolizing a blood vessel by delivering via a catheter into said blood vessel a composition comprising:
   (a) from about 2.5 to about 8.0 weight percent of a biocompatible polymer;
   (b) from about 10 to about 40 weight percent of a water insoluble, biocompatible contrast agent having an average particle size of about 10 μm or less; and
   (c) from about 52 to about 87.5 weight percent of a biocompatible solvent
   wherein the weight percent of the polymer, contrast agent and biocompatible solvent is based on the total weight of the complete composition
   under conditions wherein a precipitate is formed which embolizes the blood vessel.

10. The method according to claim 9 wherein said biocompatible solvent is selected from the group consisting of dimethylsulfoxide, ethanol, and acetone.

11. The method according to claim 10 wherein said biocompatible solvent is DMSO.

12. The method according to claim 9 wherein said water insoluble contrast agent is selected from the group consisting of tantalum, tantalum oxide, tungsten, and barium sulfate.

13. The method according to claim 9 wherein said biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

14. The method according to claim 9 wherein said biocompatible polymer is an ethylene and vinyl alcohol copolymer.

15. The method according to claim 14 wherein said contrast agent has an average particle size of from 1 to 10 microns.

16. A composition comprising:
   (a) a biocompatible prepolymer;
   (b) a water insoluble biocompatible contrast agent having an average particle size of about 10 μm or less; and
   (c) a biocompatible solvent.

17. The composition according to claim 16 wherein said water insoluble contrast agent is selected from the group consisting of tantalum, tantalum oxide, tungsten and barium sulfate.

18. The composition according to claim 17 wherein said contrast agent is tantalum.

19. The composition according to claim 16 wherein said biocompatible prepolymer is selected from the group consisting of cyanoacrylates, hydroxyethyl methacrylate, and silicone prepolymers.

20. The composition according to claim 19 wherein said biocompatible prepolymer is a cyanoacrylate.

21. The composition according to claim 20 wherein said contrast agent has an average particle size of from 1 to 10 microns.

22. The composition according to claim 16 which further comprises a biocompatible solvent.

23. The composition according to claim 22 wherein said biocompatible solvent is selected from the group consisting of dimethylsulfoxide, acetone and ethanol.

24. A method for embolizing a vascular site by delivering via a catheter into said blood vessel a composition comprising:

(a) a biocompatible prepolymer;

(b) a biocompatible water insoluble contrast agent having an average particle size of about 10 µm or less; and (c) optionally a biocompatible solvent wherein said delivery is conducted under conditions wherein said prepolymer polymerizes in situ at said vascular site thereby embolizing the blood vessel and further wherein said non-particulate agent is encapsulated within said polymer.

25. The method according to claim 24 wherein said water insoluble contrast agent is selected from the group consisting of tantalum, tantalum oxide, tungsten and barium sulfate.

26. The method according to claim 25 wherein said contrast agent is tantalum.

27. The method according to claim 24 wherein said biocompatible prepolymer is selected from the group consisting of cyanoacrylates, hydroxyethyl methacrylate, and silicone prepolymers.

28. The method according to claim 27 wherein said biocompatible prepolymer is a cyanoacrylate.

29. The method according to claim 25 wherein said contrast agent has an average particle size of from 1 to 10 microns.

30. The method according to claim 25 wherein said biocompatible solvent is selected from the group consisting of dimethylsulfoxide, acetone and ethanol.

31. A kit of parts comprising:

(a) a polymer composition comprising a biocompatible polymer, a biocompatible solvent and a water insoluble, biocompatible contrast agent having an average particle size of about than 10 µm or less; and (b) a catheter.

32. The kit of parts according to claim 31 wherein said biocompatible solvent is selected from the group consisting of dimethylsulfoxide, ethanol and acetone.

33. The kit of parts according to claim 32 wherein said biocompatible solvent is dimethylsulfoxide.

34. The kit of parts according to claim 31 wherein said water insoluble contrast agent is selected from the group consisting of tantalum, tantalum oxide, tungsten and barium sulfate.

35. The kit of parts according to claim 34 wherein said contrast agent is tantalum.

36. The kit of parts according to claim 31 wherein said biocompatible polymer is selected from the group consisting of cellulose acetates, ethylene vinyl alcohol copolymers, hydrogels, polyacrylonitrile, polyvinylacetate, cellulose acetate butyrate, nitrocellulose, copolymers of urethane/carbonate, copolymers of styrene/maleic acid, and mixtures thereof.

37. The kit of parts according to claim 36 wherein said biocompatible polymer is an ethylene and vinyl alcohol copolymer.

38. The kit of parts according to claim 37 wherein said contrast agent has an average particle size of from 1 to 10 microns.

39. The kit of parts according to claim 31 which further comprises a microballoon catheter to attenuate or arrest blood flow.

40. A kit of parts comprising:

(a) a prepolymer composition comprising a biocompatible prepolymer, a water insoluble biocompatible contrast agent having an average particle size of about 10 µm or less, and, optionally, a biocompatible solvent; and (b) a catheter.

41. The kit of parts according to claim 40 wherein said water insoluble contrast agent is selected from the group consisting of tantalum, tantalum oxide, tungsten and barium sulfate.

42. The kit of parts according to claim 41 wherein said contrast agent is tantalum.

43. The kit of parts according to claim 40 wherein said biocompatible prepolymer is selected from the group consisting of cyanoacrylates, hydroxyethyl methacrylate, and silicone prepolymers.

44. The kit of parts according to claim 43 wherein said biocompatible prepolymer is a cyanoacrylate.

45. The kit of parts according to claim 40 wherein said contrast agent has an average particle size of from 1 to 10 microns.

46. The kit of parts according to claim 40 which further comprises a microballoon catheter to attenuate or arrest blood flow.

* * * * *